US00PP26969P3

(12) United States Plant Patent
Lintott et al.

(10) Patent No.: US PP26,969 P3
(45) Date of Patent: Jul. 19, 2016

(54) ***GAILLARDIA* PLANT NAMED 'CELEBRATION'**

(50) Latin Name: *Gaillardia×grandiflora*
Varietal Denomination: Celebration

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 79 days.

(21) Appl. No.: 14/544,056

(22) Filed: Nov. 19, 2014

(65) Prior Publication Data

US 2015/0150177 P1 May 28, 2015

Related U.S. Application Data

(60) Provisional application No. 61/963,168, filed on Nov. 25, 2013.

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new cultivar of *Gaillardia* named 'Celebration' that is distinguishable by a long blooming period, compact habit and large single inflorescences composed of one row of deep red ray florets surrounding a disc whose disc and disc florets are entirely red when the inflorescence is fully developed, is disclosed.

2 Drawing Sheets

Genus and species: *Gaillardia×grandiflora*.
Variety denomination: 'Celebration'.

BACKGROUND

The present invention relates to a new and distinct cultivar of *Gaillardia* plant, also known as a blanket flower, a herbaceous perennial that is grown for use as an ornamental landscape and container plant. The new variety is known botanically as *Gaillardia×grandiflora* and will be referred to hereinafter by the variety name 'Celebration'. *Gaillardia* is in the family Compositae, under which the commonly referred to "flower" is actually the inflorescence, and made up of smaller ray florets and disc florets. The ray florets themselves have the appearance of petals.

'Celebration' originated and was selected from a large population of hybrid seedlings from a *Gaillardia* breeding program which was started by the inventors in 2006. The breeding program was conducted in a greenhouse nursery in West Sussex, United Kingdom. The aims of the breeding program were to produce novel combinations of flower colors and flower forms which are borne on well-branched plants with sturdy growth habits. The controlled hybridization was carried out using combinations of selected named varieties and selected unnamed and unreleased seedlings retained from previous breeding cycles. The hybridization which led to the selection of 'Celebration' was carried out during 2007 using *Gaillardia* 'Burgunder' (unpatented) as the male parent and a proprietary unreleased *Gaillardia* seedling known as 'G5' (unpatented) as the female parent. 'Celebration' was selected in 2009 for its bright red ray flowers, which are produced continually from May through November in the United Kingdom. 'Celebration' was also selected for its compact mounding habit and clean dark green foliage.

Asexual reproduction of the new cultivar 'Celebration' was first accomplished in October 2009. The method of asexual propagation used was shoot cuttings taken from the lateral branches of plants which were growing in an unheated greenhouse in West Sussex, United Kingdom. Subsequent asexual propagations have been carried out in the same greenhouse using both vegetative cuttings and root cuttings. 'Celebration' has been determined to be stable and reproduces true to type in successive generations of asexual reproduction by both vegetative cuttings and root cuttings.

SUMMARY

The following traits have been repeatedly observed and represent the distinguishing characteristics of 'Celebration'. 'Celebration' has not been tested under all possible conditions and phenotypic differences may be observed with variations in environmental, climatic, and cultural conditions, without however, any variance in genotype.

1. 'Celebration' exhibits a compact and naturally branching plant habit.
2. 'Celebration' exhibits large single inflorescences composed of one row of deep red ray florets.
3. The disc of a fully expanded inflorescence of 'Celebration' is comprised entirely of red disc florets.
4. 'Celebration' blooms continually from early spring until late fall.
5. After one year's growth in a 3 liter container, 'Celebration' is 35 cm to 40 cm in height and 40 cm to 45 cm in width.
6. 'Celebration' is hardy in USDA zone 5.

DESCRIPTION OF THE PHOTOGRAPHS

The accompanying color photographs illustrate the overall appearance of the new *Gaillardia* cultivar 'Celebration' showing the colors as true as it is reasonably possible to obtain in colored reproductions of this type. Colors in the photographs may differ from the color values cited in the detailed botanical description, which more accurately describes the actual colors of the new variety 'Celebration'.

DESCRIPTION OF THE NEW VARIETY

Figure 1:
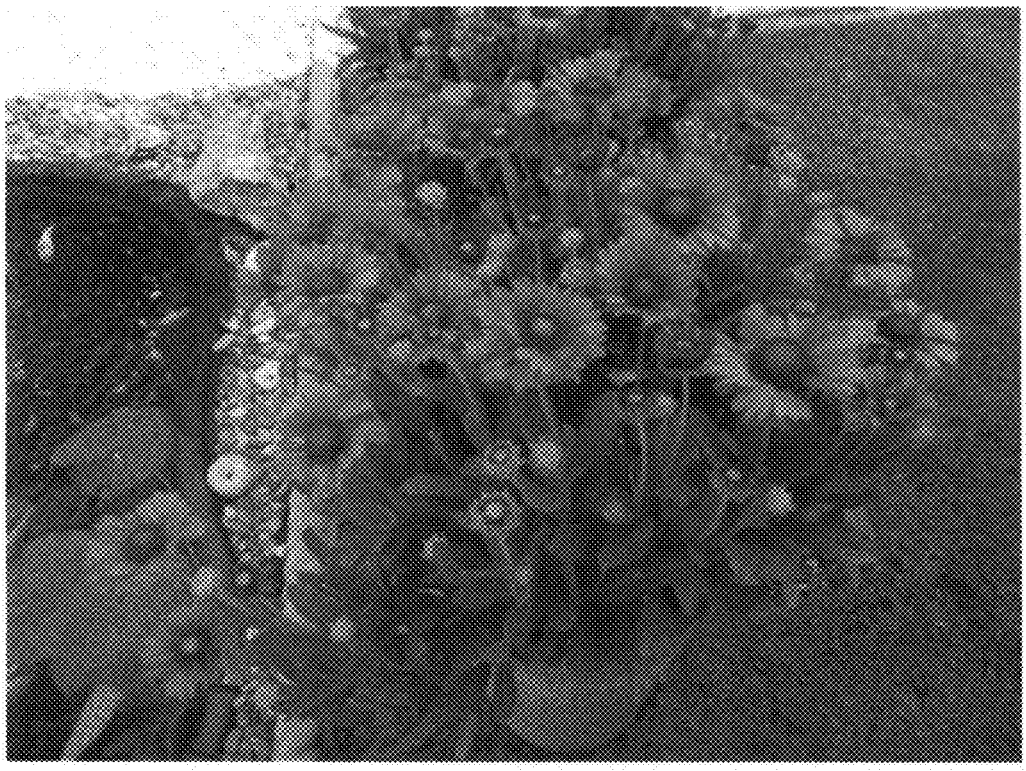
FIG. 1 depicts a whole plant of 'Celebration' which has been grown in a frost-free greenhouse in West Sussex, United Kingdom. The illustrated plant is one year old and has been grown without any pinching or chemical growth regulator.
Figure 2:
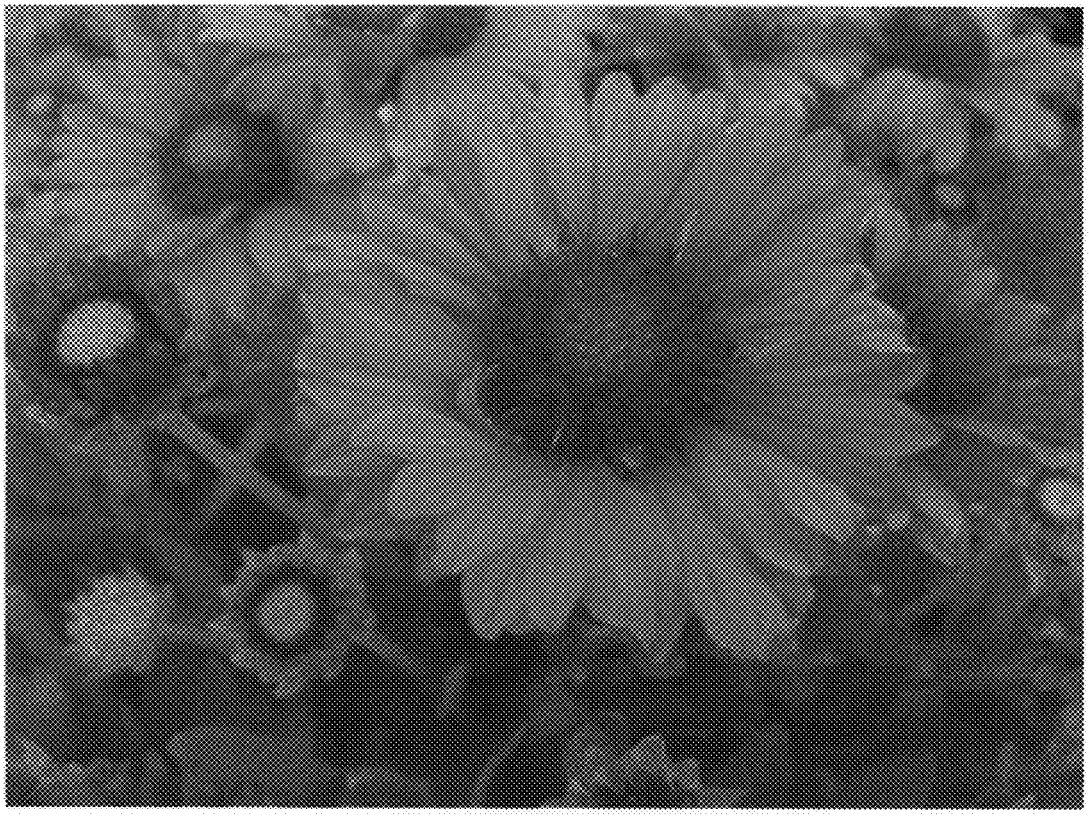
FIG. 2 depicts a close up view of the fully expanded inflorescence of 'Celebration'.

The following detailed descriptions set forth the distinctive characteristics of 'Celebration'. Observations, measurements, values, and comparisons were collected in August, 2014 in Santa Barbara, Calif. from a fifteen month old plant grown outdoors in full sun in a 3 gallon container. Color determinations were made in accordance with The 2007 Royal Horticultural Society Colour Chart from London England, except where general color terms of ordinary dictionary significance are used.

Classification:

*Family.*—Compositae.

*Genus.*—*Gaillardia.*

*Species.*—×*grandiflora.*

*Common name.*—Blanket flower.

Parentage:

*Male parent.*—*Gaillardia* 'Burgunder' (unpatented).

*Female parent.*—An unreleased *Gaillardia* seedling of proprietary origin, code number 'G5' (unpatented).

Plant:

*Propagation method.*—Typically by softwood cuttings although root cuttings have also been successful.

*Rooting system.*—Fine and fibrous.

*Vigor.*—Moderate vigor.

*Time to develop roots.*—14 to 20 days are needed for an initial cutting to develop roots.

*Temperature to develop roots.*—The recommended air temperature is 20 to 21° Centigrade.

*Crop time.*—Approximately 10 weeks to 2 months are needed to produce a 15-centimeter container from a rooted cutting.

*Growth habit.*—Compact and naturally freely branching.

*Suggested container size.*—15-centimeter container.

*Use.*—Ornamental for use as a landscape plant or container plant.

*Type.*—Herbaceous perennial.

*Overall dimensions.*—After one year's growth in a 3 liter container: 35 cm to 40 cm in height and 40 cm to 45 cm in width; at maturity in the ground: 40 cm to 45 cm in height and 50 cm to 55 cm in width.

*Cultural requirements.*—Grow in full sun with moderate water, and well-draining soil such as loam.

*Hardiness.*—USDA Zone 5.

*Growing requirements.*—If grown outside in regions which experience winter freezing, 'Celebration' may be started as a cutting during the spring or summer of the previous year, planted out prior to the onset of winter, and flowering will commence typically in May or June according to the region and season. When grown outside in frost-free regions, or in frost-protected greenhouses, 'Celebration' will flower virtually all year round and may be started as a cutting (which should be non-flowering) at any time of year.

Stems:

*Branching habit.*—Basal branching.

*Stem color.*—138B.

*Stem dimensions.*—10 cm to 15 cm in length and 5 mm in width.

*Stem shape.*—Cylindrical, slightly fluted longitudinally.

*Stem surface.*—Markedly villous with dense coverage of very fine silvery hairs, approximately 3 mm to 4 mm in length.

*Internode length.*—Average internode length is 10 mm to 12 mm.

Foliage:

*Type.*—Evergreen.

*Leaf arrangement.*—Alternate.

*Margin.*—Entire.

*Leaf shape.*—Oblanceolate.

*Leaf dimensions* (*base of plant*).—20 m to 23 cm in length, 3.5 cm in width.

*Leaf dimensions* (*at inflorescence height*).—8 cm to 9 cm in length, 2 cm in width.

*Leaf base.*—Truncate.

*Leaf apex.*—Rounded.

*Leaf attachment.*—Sessile.

*Leaf color* (*both surfaces*).—138A.

*Leaf venation pattern.*—Parallel; mid vein protrudes on both surfaces.

*Vein color* (*both surfaces*).—138B.

*Leaf surface* (*both surfaces*).—Pubescent, very fine silvery hairs, lighter than 156D, approximately 3 mm in length.

*Fragrance.*—A slight sage-like scent when bruised.

Inflorescence:

*Inflorescence.*—Solitary.

*Aspect.*—Facing upward.

*Dimensions of inflorescence.*—70 mm in diameter and 15 mm in height.

*Inflorescence type.*—Radiate capitate with central disc.

*Disc diameter* (*inflorescence fully expanded*).—27 mm to 30 mm.

*Inflorescence number per plant.*—Very numerous, a mature one-year old plant bears approximately 100 inflorescences in bud and flower at one time.

*Blooming season.*—Spring, summer and fall.

*Lastingness of inflorescence on the plant.*—10 days, reducing to 7 days in full sun in mid-summer.

Peduncle:

*Peduncle dimensions.*—8 cm to 11 cm in length and 2.5 mm in diameter.

*Peduncle shape.*—Cylindrical.

*Peduncle surface.*—Surface is pubescent and exhibits longitudinal ridges.

*Peduncle color.*—191B.

*Peduncle strength.*—Stiff.

Flower buds:

*Bud shape.*—Rotate whorl.

*Bud dimensions.*—13 mm in diameter and 8 cm in length.

*Bud color.*—145A.

*Bud surface texture.*—Villous.

Ray florets:

*Ray floret shape.*—Fan shaped with 3 fused petals appearing as lobes.

*Ray floret surface* (*outer surface*).—Pubescent.

*Ray floret surface* (*inner surface*).—Glabrous.
*Ray floret arrangement.*—Radiate.
*Number of ray florets per inflorescence.*—18 to 20 ray florets per inflorescence.
*Number of petals per ray floret.*—Three.
*Fused or unfused.*—Petals are basally fused.
*Petal margins of ray florets.*—Entire.
*Ray floret dimensions.*—3.0 cm in length including the corolla tube, 14 mm in width at the widest point.
*Corolla tube dimensions.*—5 mm in depth and 0.5 mm in diameter.
*Color of ray florets* (*inflorescence newly opening*).—Adaxial surface: 45A.
*Color of ray florets* (*inflorescence newly opening*).—Abaxial surface: N34B.
*Color of ray florets* (*inflorescence fully expanded*).—Adaxial surface: 45B, becoming 34A towards and at apex.
*Color of ray florets* (*inflorescence fully expanded*).—Abaxial surface: 32B.
*Ray floret veins* (*both surfaces*).—Longitudinal, parallel, fine but prominent; color N200B.
*Self-cleaning or persistent.*—Self-cleaning.

Disc florets:
*Quantity of disc florets per inflorescence.*—Numerous, approximately 400 to 500.
*Disc floret dimensions* (*including pistil length*).—12 mm in length and 2 mm in width.
*Corolla tube.*—Comprised of 6 longitudinally fused petals.
*Depth of corolla tube.*—5 mm in depth.
*Surface of disc florets.*—Lanate.
*Color of disc florets* (*inflorescence newly opening, both surfaces*).—Ranges between 163A and 17A, gradually becoming N34C as the inflorescence expands.
*Color of disc flowers* (*inflorescence fully expanded, both surfaces*).—N34C, apex N34A.
*Pappus* (*sepals*).—6 in number, lanceolate, fused at base, apex aristate.
*Pappus color.*—157D, translucent.
*Phyllary dimensions.*—3 cm in diameter and 1 cm in length.
*Phyllary color.*—137A.
*Phyllary arrangement.*—Whorl of involucral bracts arranged in 3 rows of 8 to 10 bracts per row.
*Number of involucral bracts.*—An average of 25 in number per inflorescence.
*Shape of involucral bract.*—Oblanceolate.
*Involucral bract dimensions* (*maximum*).—16 mm in length and 5 mm in width.
*Involucral bract margin.*—Entire.
*Involucral bract apex.*—Acuminate.
*Involucral bract base.*—Truncate.
*Involucral bract color* (*both surfaces*).—137A.
*Involucral bract surface* (*both surface*).—Pubescent.
*Fragrance of inflorescence.*—Sweet fragrance, reminiscent of citrus.

Reproductive organs:
*Stamens* (*present on disc florets only*).—Three in number, adnate to inner surface of corolla tube.
*Stamen dimensions.*—2 mm in width and 5 mm in length.
*Stamen color.*—N34C.
*Anther dimensions.*—2 mm in length and less than 0.25 mm in width.
*Anther color.*—59A.
*Anther shape.*—Very narrow lanceolate.
*Pollen.*—Present.
*Quantity of pollen.*—Large amount.
*Pollen color.*—17C.
*Style dimensions.*—7 mm in length and 1 mm in width.
*Style color.*—21B.
*Stigma dimensions.*—5 mm in length and less than 0.5 mm in width.
*Stigma color.*—59A.
*Stigma shape.*—Bifurcate, decurrent.
*Ovary position.*—Inferior.
*Ovary color.*—157D.
*Ovary shape.*—Obconical.
*Ovary dimensions.*—2.5 mm in width and 3.5 mm in height.

Fruit/seed set:
*Number of seeds.*—Small to moderate amount (ranges from 50 to 100 seeds per inflorescence).
*Seed dimensions.*—5 mm to 6 mm in length (including hairs at apex) and 1 mm to 2 mm in diameter.
*Seed color.*—200A.
*Seed shape.*—Conical with rounded base and apex.
*Seed surface.*—Smooth except at apex where many very fine silver hairs, up to 2 mm in length, are present in circular groups.

Disease and pest susceptibility: 'Celebration' has not been observed to exhibit any resistance to any particular pest or disease. 'Celebration' is susceptible to downy mildew and to thrips as may be typical of *Gaillardia*.

COMPARISON WITH PARENTAL LINES AND KNOWN VARIETY

'Celebration' is distinguishable from the female parent, 'G5' as follows. Whereas the female parent exhibits red-bronze colored flowers, the flowers of 'Celebration' are bright red in color. 'Celebration' is more floriferous and exhibits a more compact plant habit than the female parent.

'Celebration' is distinguishable from the male parent, 'Burgunder' as follows. Whereas the male parent exhibits wine-red almost purple colored flowers, the flowers of 'Celebration' are bright red in color. Additionally, the male parent exhibits a double row of petals while 'Celebration' exhibits a single row of petals.

The variety of *Gaillardia* which most closely resembles 'Celebration' is the variety, 'Burgunder' (unpatented). 'Celebration' exhibits bright red colored flowers, while 'Burgunder' exhibits wine red and almost purple colored flowers. Additionally, 'Celebration' bears many more flowers than "Burgunder' and exhibits a more compact plant habit.

We claim:

1. A new and distinct cultivar of *Gaillardia* plant named 'Celebration' as described and illustrated herein.

* * * * *